March 8, 1955 E. G. FISHER Plant Pat. 1,360
ROSE PLANT
Filed June 10, 1954
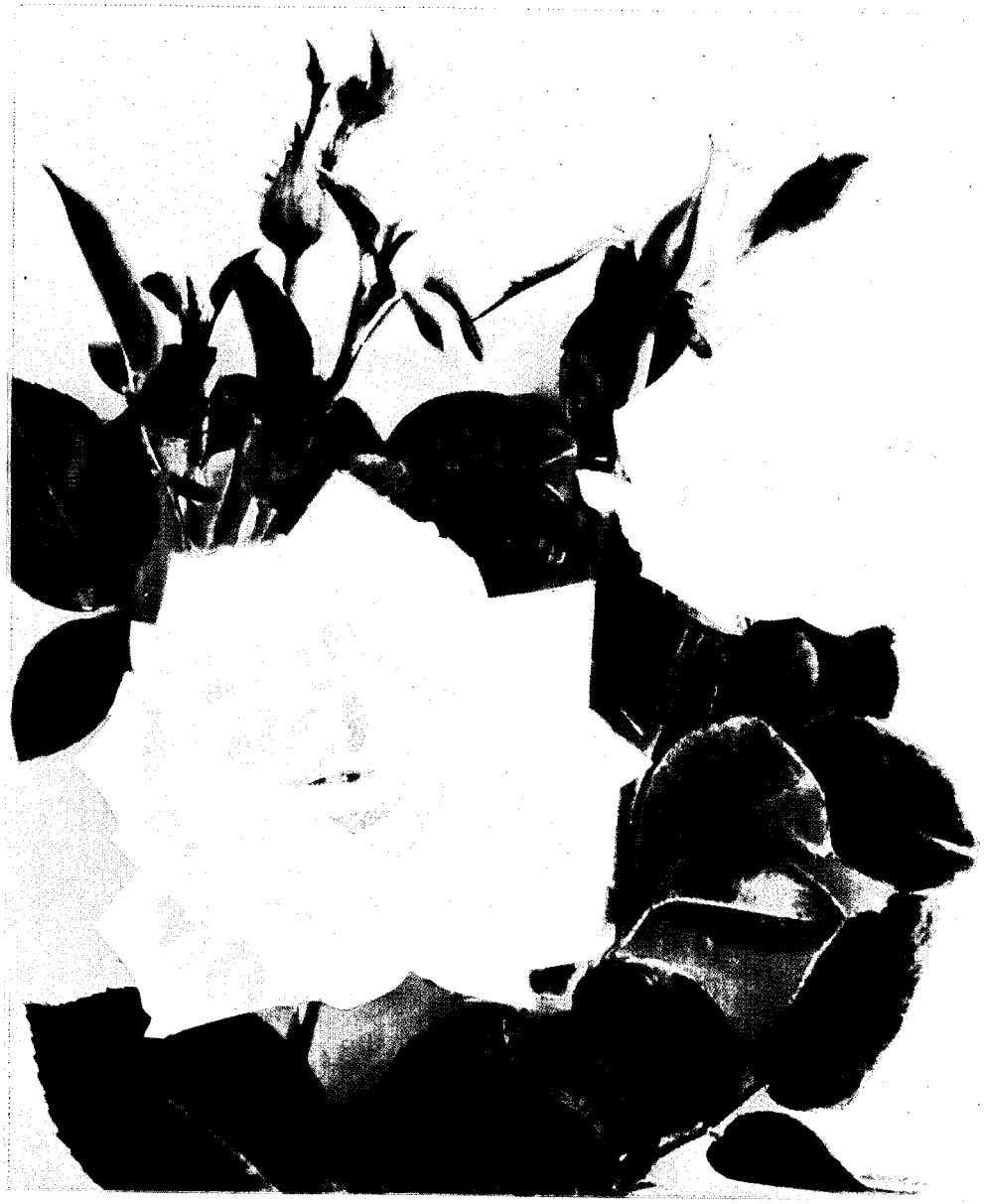
Inventor.
Esther Gladys Fisher
By: Cobb & Cobb
Attorneys.

United States Patent Office

Plant Pat. 1,360

Patented Mar. 8, 1955

1,360

ROSE PLANT

Esther Gladys Fisher, Woburn, Mass., assignor, by mesne assignments, to The Conard-Pyle Company, West Grove, Pa., a corporation of Pennsylvania Application June 10, 1954, Serial No. 435,960

1 Claim. (Cl. 47—61)

The present invention relates to a new and distinct variety of rose plant of the hybrid tea class, which was originated by me by crossing the variety "Peace" (Plant Patent No. 591) with the variety "Orange Nassau" (Plant Patent No. 350).

As the result of this breeding, I have produced a new rose variety which is primarily characterized as to novelty by the distinctive color of its mature blooms, the general color effect of which is Rose Neyron on the inner surfaces of the petals, and Cream Color on the outer surfaces of the petals. The blooms of my new variety are also characteristically larger than those of other bi-color varieties grown under comparable conditions, and accordingly, my new variety represents a unique and most desirable combination of features which distinguishes the new variety from its parents, as well as from all other varieties of its class.

Asexual reproduction of my new variety, as performed by me by budding, at Woburn, Massachusetts, and as also performed at West Grove, Pennsylvania, shows that the foregoing characteristics and distinctions come true to form and are established and transmitted through succeeding propagations.

The accompanying drawing shows typical specimens of the flowers and foliage of my new variety in different stages of development and depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway") and the Royal Horticultural Society Color Chart (hereinafter abbreviated as "Royal"), as indicated, except where general color terms of ordinary dictionary significance are obvious:

Type: Hardy bush; outdoor; seedling; for cut-flowers and for garden decoration.
Class: Hybrid tea.
Breeding: Seedling.
*Seed parent.*—"Peace."
*Pollen parent.*—"Orange Nassau."
Propagation: Holds its distinguishing characteristics through succeeding propagations by budding.

FLOWER

Locality where grown and observed: West Grove, Pennsylvania.
Flowers borne: Singly; on medium length stems of normal strength.
Quantity of bloom: Free, outdoors.
Continuity: Continuous.
Fragrance: Moderate to strong.
Bud:
*Peduncle.*—Medium length; medium caliper; erect; rough; medium number of Brown prickles. Color—Hazel, Plate XIV (Ridgway).
*Before calyx breaks.*—Size—large. Form—medium length; ovoid; with a conspicuous neck; with foliaceous appendages on the surface of the bud; with medium size, little-cut, bristle-like foliaceous parts extending beyond the tip of the bud equal to ¼ or more of its length.
*As calyx breaks.*—Color—Poupre Carmine, Tone 1, Plate 156 (Royal) where exposed to sun; Lime Green Plate XXXI (Ridgway) at edges of sepals.
*As first petal opens.*—Size—medium. Form—ovoid.

Color: outside—Buff Yellow, Plate IV (Ridgway), blotched irregularly with Begonia Rose, Plate I (Ridgway); inside—Begonia Rose, Plate I (Ridgway), with blotches of Solferino, Tone 2, Plate 157 (Royal), shading to Rouge Coccine, Tone 1, Plate 83 (Royal), then sharply to Lemon Chrome, Plate IV (Ridgway), to Light Cadmium, Plate IV (Ridgway), and then to Lemon Chrome, Plate IV (Ridgway).
*Opening.*—Opens up well.
Bloom:
*Size (when fully open).*—Large; from 4½ inches to 5 inches.
*Petalage.*—Double; from 35 to 54 petals; arranged regularly.
*Form.*—Cupped at first and remaining cupped; petals being at first loosely rolled outward and remaining loosely rolled outward through maturity.
Petals: Medium thickness; with inside satiny and outside satiny.
*Shape.*—Outer petals—obovate, with 1 notch. Intermediate petals—obovate, with 1 notch. Inner petals—obovate; irregular; sometimes with 1 notch and sometimes with 2 notches.

This description of a newly opened flower was made from a rose grown outdoors in the month of September, at West Grove, Pennsylvania:

Color:
*Outer petal.*—Outside surface—Naples Yellow, Plate XVI (Ridgway), shading to Citron Yellow, Plate XVI (Ridgway), and then to Lemon Chrome, Plate IV (Ridgway). Inside surface—Rose Neyron, Tone 3, Plate 119 (Royal), with veining of Rose Neyron, Tone 4, Plate 119 (Royal); lower quarter of petals change abruptly to Picric Yellow, Plate IV (Ridgway), and then to Lemon Chrome, Plate IV (Ridgway); occasional streaks of Picric Yellow, Plate IV (Ridgway) may run to outer margin of petal.
*Intermediate petal.*—Outside surface—Maize Yellow, Plate IV (Ridgway), shading to Buff Yellow, Plate IV (Ridgway), and then to Empire Yellow, Plate IV (Ridgway). Inside surface—Carmine Passé, Tone 1, Plate 107 (Royal), shading to Rouge Andrinople, Tone 2, Plate 92 (Royal); basal quarter of petal changes abruptly to Lemon Yellow, Plate IV (Ridgway), and then to Lemon Chrome, Plate IV (Ridgway).
*Inner petal.*—Outside surface—Maize Yellow, Plate IV (Ridgway), shading to Pinard Yellow, Plate IV (Ridgway), and then to Pale Lemon Yellow, Plate IV (Ridgway). Inside surface—Rose Neyron, Tone 3, Plate 119 (Royal), running abruptly into Lemon Yellow, Plate IV (Ridgway), and then into Lemon Chrome, Plate IV (Ridgway).

This description was made from a rose that was open for three days outdoors in the month of September, at West Grove, Pennsylvania:

Color:
*Outer petal.*—Outside surface—Pale Purplish Vinaceous, Plate XXXIX (Ridgway), shading into Chalcedony Yellow, Plate XVII (Ridgway), and then to Citron Yellow, Plate XVI (Ridgway). Inside surface—Rose Neyron, Tone 2, Plate 119 (Royal), passing sharply into Martius Yellow, Plate IV (Ridgway), and then into Lemon Yellow, Plate IV (Ridgway).
*Inner petal.*—Outside surface—Cartridge Buff, Plate XXX (Ridgway), shading to Cream Color, Plate XVI (Ridgway), then to Pinard Yellow, Plate IV (Ridgway), and to Empire Yellow, Plate IV (Ridgway) at base. Inside surface—Rose Neyron, Tone 1, Plate 119 (Royal), changing to Picric Yellow, Plate IV (Ridgway), and to Empire Yellow, Plate IV (Ridgway) at base.
*General color effect.*—Newly opened flower—inner surfaces of petals are Rose Neyron, Tone 3, Plate 119 (Royal), with outer surfaces generally Maize Yellow, Plate IV (Ridgway). 3-days open—Rose Neyron, Tone 2, Plate 119 (Royal) on inner surfaces of petals, with Cream Color, Plate XVI (Ridgway) on outer surfaces, but sometimes showing suffusion of Pink.

*Behavior.*—Persist.

*Flower longevity.*—On bush in garden—4 or 5 days in September. Cut roses grown outdoors and kept at living-room temperatures—4 days in September.

REPRODUCTIVE ORGANS

Stamens: Arranged regularly about pistils.

Filaments: Many; most with anthers; medium length. Color—Lemon Chrome, Plate IV (Ridgway).

Anthers: All open at once; medium size; seldom an anther fused with a petaloid. Color—Lemon Chrome, Plate IV (Ridgway).

Pollen: Moderate abundance. Color—Primuline Yellow, Plate XVI (Ridgway).

Pistils: Medium number.

Styles: Uneven; medium length; medium caliper; bunched.

Stigma: Color—Amber Yellow, Plate XVI (Ridgway).

Ovaries: Some protruding from calyx.

Hips: None.

Sepals: Permanent; medium length; spear-shaped.

Seeds: None.

PLANT

Foliage:

*Leaves.*—Usually compound of 5, but sometimes of 7 leaflets; normal abundance; medium size; thin; slightly glossy.

*Leaflets.*—Shape—ovoid, with apex acute. Base—round. Margin—simply serrate.

*Color.*—Mature: Upper surface—Cedar Green, Plate VI (Ridgway); under surface—Asphodel Green, Plate XLI (Ridgway). Young: Upper surface—Cerro Green, Plate V (Ridgway), suffused and bordered by Hay's Maroon, Plate XIII (Ridgway); under surface—Dark Vinaceous, Plate XXVII (Ridgway).

*Rachis (the supporting stem of the compound leaf).*—Medium caliper. Upper side—grooved and hairy. Under side—sparsely thorny.

*Stipules.*—Short; medium width; with short points turning out at an angle of more than 90°.

*Disease resistance.*—Normally resistant to mildew and blackspot, as compared with other varieties grown under comparable cultural conditions at West Grove, Pennsylvania.

Growth:

*Habit.*—Bushy; much-branched.

*Growth.*—Free.

*Canes.*—Medium caliper.

*Main stems.*—Color—Light Hellebore Green, Plate XVII (Ridgway). Thorns — several; medium length; hooked downward; with medium length, oval base. Prickles — several; color — bronze. Hairs—few; color—reddish.

*Branches.*—Color—Biscay Green, Plate XVII (Ridgway). Thorns—several; straight; pointed downward; with medium length, oval base. Prickles—several; color—bronze. Hairs—few; color—reddish.

*New shoots.*—Color—Pompeian Red, Plate XIII (Ridgway). Thorns — several; medium length; hooked slightly downward; with medium length, oval base. Prickles — several; color — reddish. Hairs—none.

I claim:

A new and distinct variety of rose plant of the hybrid tea class, substantially as herein shown and described, characterized particularly as to novelty by the relatively large size of its blooms, and by the distinctive general color tonality of its bi-color blooms in their mature stage.

No references cited.